United States Patent [19]

Fuchs

[11] Patent Number: 4,682,992
[45] Date of Patent: Jul. 28, 1987

[54] MICROBICIDAL COATED BEADS

[75] Inventor: Alfred E. Fuchs, Denville, N.J.

[73] Assignee: Potters Industries, Inc., Hasbrouck Heights, N.J.

[21] Appl. No.: 624,350

[22] Filed: Jun. 25, 1984

[51] Int. Cl.⁴ .............................................. B01D 19/00
[52] U.S. Cl. ........................................ 55/279; 55/512; 55/524; 422/37; 422/120; 422/122; 514/63
[58] Field of Search ................... 55/279, 99, 524, 512; 514/63; 422/5, 37, 28, 29, 120, 122

[56] References Cited

U.S. PATENT DOCUMENTS

| 2,460,977 | 2/1949 | Davis et al. | |
|---|---|---|---|
| 2,461,011 | 2/1949 | Taylor et al. | |
| 2,739,906 | 3/1956 | Berry et al. | |
| 2,765,046 | 10/1956 | Rondholz | 55/279 |
| 3,116,969 | 1/1964 | Coleman | 55/279 |
| 3,558,345 | 1/1971 | Baum et al. | |
| 3,589,106 | 6/1971 | Onuki | 55/524 |
| 3,617,333 | 11/1971 | Brown | |
| 3,661,628 | 5/1972 | Marsden | |
| 3,680,287 | 8/1972 | Wood et al. | 55/524 |
| 3,820,308 | 6/1974 | Onuki | 55/524 |
| 4,419,107 | 12/1983 | Roydhouse | 55/99 |
| 4,475,931 | 10/1984 | Clift et al. | 55/99 |

FOREIGN PATENT DOCUMENTS

| 1335660 | 7/1963 | France | 55/512 |
|---|---|---|---|
| 1347870 | 11/1963 | France | 55/512 |
| 708155 | 4/1954 | United Kingdom | |
| 833180 | 4/1960 | United Kingdom | |
| 846458 | 8/1960 | United Kingdom | 55/279 |
| 1433303 | 4/1976 | United Kingdom | |

OTHER PUBLICATIONS

Gettings and Triplett, "A New Durable Antimicrobial Finish for Textiles".
Siddiqui, Malek, and Hobbs, "Percutaneous Absorption of an Antimicrobial Organosilican Quarternary Ammonium Chloride in Rabbits".
Dow Corning, Information About Antimicrobial Agents.
Yoshihiro Nakagawa et al., "Disinfection of Water with Quaternary Ammonium Salts Insolubilized on a Porous Glass Surface", Applied and Environmental Microbiology, Mar., 1984, pp. 513-518.
An advertisement of Dow Corning Corp.
A Plastics Compounding Article.

Primary Examiner—Bernard Nozick
Attorney, Agent, or Firm—Lee C. Robinson, Jr.

[57] ABSTRACT

Organosilicon quaternary ammonias and other microbicidal compounds are bound to the surface of discrete inorganic particles such as glass spheres. Inorganic particles coated with the microbicidal compounds are used in hospital fluidized beds, air filters, and other products in which microbicidal qualities are desired.

20 Claims, 2 Drawing Figures

4,682,992

MICROBICIDAL COATED BEADS

BACKGROUND OF THE INVENTION

This invention relates to microbicidal coatings for discrete inorganic particles such as glass beads. Such coatings impart to their substrates a microbicidal effect, rendering those substrates and products made therefrom highly advantageous for use wherever sterile conditions are desired. Such uses include but are not limited to coating of substrates used in hospital fluidized beds and coating of substrates used in fibers for air filtration.

It is known that most microbicidal agents, to be effective, must penetrate the cell structure of the microbes they destroy. This means that most microbicidal agents would lose their effectiveness if they were surface hindered, that is, if they were attached to the surface of a substrate such that they could not be absorbed into the cell structure of attacked microbes. However agents which are not surface hindered are lost from the substrate over a period of time such that the microbicidal property of the substrate is diminished and cannot be regenerated.

Isquith et al. reported in the December, 1972 issue of *Applied Microbiology*, at pages 859–863, that the hydrolysis product of 3-(trimethoxysilyl)-propyldimethyloctadecyl ammonium chloride exhibited microbicidal activity against a broad range of microorganisms while chemically bonded to a variety of surfaces. However, Isquith et al. treated only large single surfaces with their microbicidal compound, and did not undertake to ascertain the effectiveness of other surface hinderable microbicidal compounds which might be desirable for us in particular products.

SUMMARY

It has now been found that a wide variety of useful products can be rendered microbicidal over long periods by coating small component fibers and particles of the product with any of a number of surface hinderable microbicidal agents. These agents are preferably organosilicon quaternary ammonium compounds. The specific compounds selected will vary with any secondary characteristics which it may be desirable to impart to the final product. For instance, microbicidal beads of the invention, when used in hospital fluidized beds, are preferably coated with an agent which is hydrophobic since moisture resistance is desired in the final product.

It is accordingly an object of the present invention to provide a wide variety of surface hinderable microbicidal compounds.

It is another object of the invention to use surface hinderable microbicidal compounds as coatings on small inorganic particles and fibers.

It is a further object of the present invention to provide large-scale microbicidal products which are comprised of small particulate substrates coated with microbicidal agents such that air can penetrate the large final products.

Another object is to impart microbicidal characteristics to large products such as air filters or fluidized beds by treating with microbicidal coatings those small particles and fibers of which the large final products are comprised.

Still another object of the invention is to provide bedding and air filters which are highly beneficial in maintaining a sterile environment, economical to manufacture and maintain, and thoroughly reliable in use.

DESCRIPTION OF CERTAIN PREFERRED EMBODIMENTS

Figure 1:
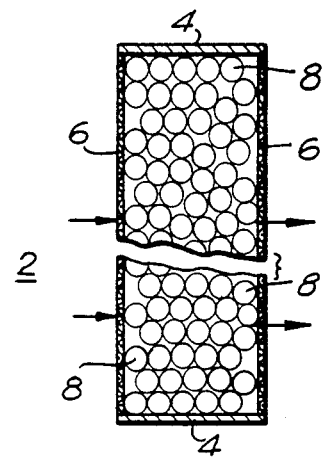
FIG. 1 is a diagramatic representation of an air filter in accordance with the present invention.

In a preferred embodiment of the invention, the substrate that is to be treated with a microbicidal agent is in the form of small glass spheres or beads ranging in size from 1 to 200 microns. Silica gels and other inorganic substrates can also be used. In this connection, a mixture of inorganic subtrates, such as a mixture of inorganic particles comprised of glass and inorganic particles comprised of silica gels, is suitable. In an advantageous embodiment the discrete inorganic particles are made up of a mixture of glass spheres and silica gel spheres.

It is initially desirable to sterilize the glass beads by any of a variety of known methods such as subjecting them to steam, dry heat over a period of several hours, or cold sterilization. A quantity of glass beads is then measured into a reaction vessel. Next, one or more appropriate microbicidal agents are selected which are capable of killing microbes while surface bound to a substrate in such a way that the agents cannot enter the body of microbes they attack. Preferred agents include but are not limited to octadecyldimethyl [3-(trimethoxysilyl) propyl ammonium chloride in organic solvent, and N-Trimethoxysilylpropyl-N,N-Trimethyl ammonium chloride in organic solvent.

A carefully measured amount of the selected microbicidal agent is measured into the reaction vessel with the glass beads. Preferably, 0.1 to 2.5 milliliters of microbicidal coating are added per 1,000 grams of glass beads to be coated, although other ratios are possible within the scope of the invention. A small quantity of water may optionally be added to dilute the coating agent.

For beads used in hospital air beds which are expected to be in a constant state of fluidization, a coating which is moisture resistant is highly preferred. It is thus desirable to add a base as a curing catalyst to impart hydrophobicity to the coating. Preferred bases for this purpose include but are not limited to secondary amines such as dipropylamine and tertiary amines such as benzyl dimethylamine. The aforementioned microbicidal agents of the invention are also capable of acting as the catalyizing base. These bases catalyze the incorporation of hydrophobic constituents into the coating. A preferred hydrophobic constituent is polymethyl hydrogen siloxane.

It is desirable to add all of the materials of the invention under agitation and to then heat the mixture for 10 to 15 minutes at a temperature no higher than 80° C.

The benefits of glass beads so treated include the reduction of bacteria not only in the final use of the beads but also in the making and handling of the beads. One of many useful functions to which the treated beads can be applied is in hospital fluidized beds, which acquire microbicidal characteristics when comprised of coated glass beads of the instant invention. Such beds are highly beneficial in preventing decubitis ulcers because the beds allow for the free penetration of air.

Beds made with beads of the instant invention not only kill bacteria within the bed, but are also capable of killing bacteria which are produced by a patient. A highly economical attribute of bedding and other products made in accordance with the instant invention is that such products can be repeatedly cleaned with a variety of solvents without experiencing appreciable loss of microbicidal effectiveness. This is true because the microbicidal coating is firmly attached to the surface of the inorganic particles of the invention. Fluidized beds of the instant invention also have beneficial sanitary and hygienic uses outside of hospital environments.

Figure 2:
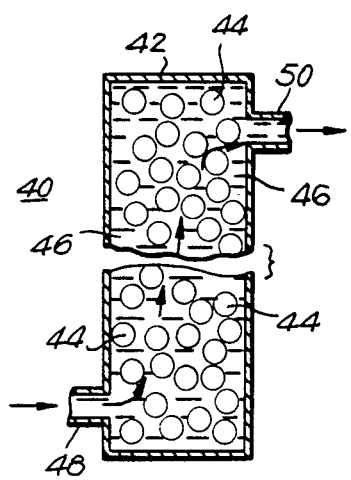
FIG. 2 is a diagramatic representation of a fluidized bed in accordance with the present invention.

In FIG. 2 there is shown one embodiment of a fluidized bed arrangement 40 in accordance with the invention. A container 42 generally encloses microbicidally coated glass spheres 44 and fluid moving through them 46. The path of fluid movement through the coated glass beads is shown by the arrows inside container 42, and indicates that fluid is injected by means of port 48 and is discharged at port 50. The movement of the fluid through the coated glass particles keeps them in a suspended state and the fluid transported through the bed is thereby rid to an advantageous extent of undesirable bacteria, etc.

The invention is broadly applicable to a wide range of products which are comprised of small particulate substrates. For instance, silica gel spheres and fibers can be coated with microbicidal agents in accordance with the current invention and incorporated into moisture-removing air filters. Air filters so constituted remove undesirable bacteria and other microbes from the air. They can also be incorporated as pre-filters to clean air used for fluidization in the fluidized beds of the invention.

In FIG. 1 is shown one embodiment of an air filter 2 in accordance with the invention. The air filter is formed of frame members 4 and perforate screens 6 which form a container to enclose microbicidally coated glass beads 8. Air flow passess through left-hand screen 6, through the microbicidally-coated beads contained between the screens (where it is cleansed to an advantage extent of undesirable bacteria, etc.) and out of the filter through right-hand screen 6. The arrows in FIG. 1 show the general direction of air-flow.

EXAMPLES

Shown below are some specific examples representing preferred embodiments of the invention. Each example merely illustrates the invention and is not intended to impose any limitation upon the scope of the invention.

EXAMPLE 1

Microbicidal coated beads for use in fluidized beds and other microbicidal products were prepared by adding the following materials and reagents to a reaction vessel in the order listed with substantial hand agitation during each successive addition, followed by agitation on a roller and heating to a temperature of not more than 80° C. for 10 to 15 minutes. The compounds and relative quantities added were as follows:
(1) 1,000 grams of glass beads with diameters of approximately 100 microns
(2) 1.0 milliliters of a solution of benzyl dimethyl amine and water in a ratio of one part amine to 7 parts water
(3) 0.5 milliliters polymethyl hydrogen siloxane
(4) 1.0 milliliters octadecyldimethyl [3-(trimethoxysilyl) propyl]ammonium chloride in 50% methanol.

EXAMPLE 2

Microbicidal coated beads were prepared as in Example 1 except that components 3 and 4 were mixed together before being introduced into the reaction vessel.

EXAMPLE 3

Microbicidal coated beads were prepared as in Example 1 wherein the components and quantities of each used were as follows:
(1) 1,000 grams of glass beads with diameters of approximately 100 microns
(2) 1.0 milliliters of a solution of benzyl dimethyl amine and water in a ratio of one part amine to 7 parts water
(3) 0.5 milliliter polymethyl hydrogen siloxane
(4) 1.0 milliliters octadecyldimethyl [3-(trimethoxysilyl) propyl]ammonium chloride in 50% methanol.

EXAMPLE 5

Microbicidal coated beads were prepared as in Example 1 wherein the components and quantities of each used were as follows:
(1) 1,000 grams of glass beads with diameters of approximately 100 microns
(2) 0.5 milliliters water
(3) 1.0 milliliters octadecyldimethyl [3-(trimethoxysilyl) propyl]ammonium chloride in 50% methanol.

EXAMPLE 6

Microbicidal coated beads were prepared as in Example 1 wherein the components and quantities of each used were as follows:
(1) 1,000 grams of glass beads with diameters of approximately 100 microns
(2) 0.5 milliliters water
(3) 0.5 milliliters octadecyldimethyl [3-(trimethoxysilyl) propyl]ammonium chloride in 50% methanol.

EXAMPLE 6

Microbicidal coated beads were prepared as in Example 1 wherein the components and quantities of each used were as follows:
(1) 1,000 grams of glass beads with diameters of approximately 100 microns
(2) 0.5 milliliters water
(3) 0.1 milliliters of octadecyldimethyl [3-(trimethoxysilyl) propyl]ammonium chloride in 50% methanol.
(4) 0.5 milliliters of polymethyl hydrogen siloxane

EXAMPLE 7

Anti-microbial coated beads were prepared as in Example 1 wherein the components and quantities of each used were as follows:
(1) 1,000 grams of glass beads with diameters of approximately 100 microns
(2) 0.5 milliliters water
(3) 0.1 milliliters octadecyldimethyl [3-(trimethoxysilyl) propyl]ammonium chloride in 50% methanol.

EXAMPLE 8

Microbicidal coated beads were prepared as in Example 1 wherein the components and quantities of each used were as follows:
(1) 1,000 grams of glass beads with diameters of approximately 100 microns
(2) 0.5 milliliters water (3) 1.0 milliliters N-trimethoxysilypropyl-N, N-trimethylammonium chloride in methanol.

The terms, expressions, compounds and relative quantities of compounds discussed in the Examples above are used as terms of description only and not as terms of limitation. There is no intention in the use of such terms, expressions, compounds or relative quantities of excluding any equivalents or portions thereof, it being recognized that various modifications are possible within the scope of the invention.

We claim:

1. A composition consisting essentially of discrete and separate minute and inorganic spheroidal particles coated with surface hindered microbicidal agents which microbicidal agents are firmly bound to the surface of the inorganic particles to provide a dry microbicidal coating on each of said particles.

2. A composition as in claim 1 wherein the surface hindered microbicidal agents are quaternary ammonium compounds.

3. A composition as in claim 1 wherein the surface hindered microbicidal agents are orgainc quaternary ammonium compounds.

4. A composition as in claim 1 wherein the surface hindered microbicidal agents are organosilicon quaternary ammonium compounds.

5. A composition as in claim 1 wherein the surface hindered microbicidal agents are quaternary ammonium 6. A composition as in claim 1 wherein the surface hindered microbicidal agents are organosilicon quaternary ammonium chlorides.

7. A composition as in claim 1 wherein the surface hindered microbicidal agents are one or more compounds selected from the group consisting of:
    (1) octadecyldimethyl [3-(trimethoxysilyl) propyl ammonium chloride in organic solvent; and
    (2) N-Trimethoxysilylpropyl-N, N-Trimethyl ammonium chloride in organic solvent.

8. A composition as in claim 1 wherein the discrete inorganic particles are comprised of glass, silica gel, or a mixture of both.

9. A composition as in claim 10 wherein the surface hindered microbicidal agents are one or more compounds selected from the group consisting of:
    (1) octadecyldimethyl [3-(trimethoxysilyl) propyl ammonium chloride in organic solvent; and
    (2) N-Trimethoxysilylpropyl-N, N-Trimethyl ammonium chloride in organic solvent.

10. A composition as in claim 1 wherein the discrete inorganic particles are glass spheres or silica gel spheres or a mixture of both.

11. A composition as in claim 10 wherein the surface hindered microbicidal agents are organic quaternary ammonium compounds.

12. A fluidized bed comprised of discrete inorganic spheroidal particles coated with surface hindered microbicidal agents, which microbicidal agents are firmly bound to the surface of the inorganic particles to provide a dry microbicidal coating on each of said particles; and
    means for directing a fluidizing gas against the thus coated particles to maintain the same in a constant state of fluidization within said bed.

13. A fluidized bed as in claim 12 wherein the fluidizing gas comprises air, and which further comprises at least one air filter communicating with said directing means, said air filter being comprised of discrete inorganic spheroidal particles coated with surface hindered microbicidal agents which are firmly bound to the surface of the inorganic particles to provide a dry microbicidal coating on each of said particles.

14. A fluidized bed as in claim 12 wherein the discrete inorganic particles are glass spheres or silica gel spheres or a mixture of both, and the biocidal compounds are organic quaternary ammonium compounds.

15. A fluidized bed as in claim 14 wherein the microbicidal agents are one or more compounds selected from the group consisting of:
    (1) octadecyldimethyl [3-(trimethoxysilyl) propyl ammonium chloride in organic solvent; and
    (2) N-Trimethoxysilylpropyl-N, N-Trimethyl ammonium chloride in organic solvent.

16. An air filter consisting essentially of discrete and separate minute inorganic spheroidal particles coated with surface hindered microbicidal agents, which microbicidal agents are firmly bound to the surface of the inorganic particles, to provide a dry microbicidal coating on each of said particles.

17. An air filter as in claim 6 wherein the discrete inorganic spheroidal particles are comprised of glass or silica gel or a mixture of both, and the microbicidal agents are organic quaternary ammonium compounds.

18. An air filter as in claim 17 wherein the microbicidal agents are one or more compounds selected from the group consisting of:
    (1) octadecyldimethyl [3-(trimethoxysilyl) propyl ammoniu.n chloride in organic solvent; and
    (2) N-Trimethoxysilylpropyl-N, N-Trimethyl ammonium chloride in organic solvent.

19. A composition which comsists essentially of, in combination:
    a multiplicity of discrete and separate inorganic spheroidal particles ranging in size from about 1 to about 200 microns; and
    a surface hindered microbidcidal coating on each of said inorganic particles, said coating being firmly bound to the surfaces of the particles to provide a dry microbicidal coating on each of said particles.

20. A composition which consists essentially of, in combination:
    a multipilicity of spheroidal glass beads ranging in size from about 1 to about 200 microns; and
    a surface hindered microbicidal coating on each of said glass beads, said coating comprising organosilicon quaternary ammonium chlorides and being firmly bound to the spherical surfaces of the beads, to provide a dry microbicidal coating on each bead.

* * * * *